United States Patent [19]

Lerner

[11] Patent Number: 4,908,318

[45] Date of Patent: Mar. 13, 1990

[54] NUCLEIC ACID EXTRACTION METHODS

[75] Inventor: Terry Lerner, Newton, Mass.

[73] Assignee: Integrated Genetics, Inc., Framingham, Mass.

[21] Appl. No.: 93,397

[22] Filed: Sep. 4, 1987

[51] Int. Cl.$^4$ ............................................... C12N 1/08
[52] U.S. Cl. ..................................... 435/270; 435/269; 536/27
[58] Field of Search ...................... 435/270; 536/76, 27

[56] References Cited

U.S. PATENT DOCUMENTS 3,433,782  3/1969  Kreiser .................................. 536/28
3,582,468  6/1971  Birnbaum ............................. 435/270

FOREIGN PATENT DOCUMENTS 1331933  9/1973  United Kingdom .

OTHER PUBLICATIONS

Kochetkov et al.—Organic Chemistry of Nucleic Acids, (Part A), (1971), Plenum Press, pp. 17 and 18.

*Primary Examiner*—Sam Rosen
*Attorney, Agent, or Firm*—Mark A. Hofer; Paul T. Clark

[57] ABSTRACT

A method of extracting nucleic acids from a crude buffy coat fraction in an aqueous medium includes the steps of treating the buffy coat fraction to break open the white blood cells to release the proteins and the nucleic acids in the cells into the aqueous medium; solubilizing the proteins and the nucleic acids in the aqueous medium; and precipitating the nucleic acids under conditions under which the proteins remain in solution.

7 Claims, No Drawings

NUCLEIC ACID EXTRACTION METHODS

BACKGROUND OF THE INVENTION

This invention relates to nucleic acid extraction methods.

A nucleic acid hybridization assay typically is performed on nucleic acids that have been isolated from cells. A common method of carrying out the isolation is the phenol extraction method.

Lizardi et al., 98 Analytical Biochem. 116 (1979), describe a method for extracting RNA from cells. The method includes the steps of treating a cell sample with, consecutively, a solution containing sodium dodecyl sulfate (SDS) and proteinase K; aqueous sodium perchlorate; and ethanolic perchlorate. The cell samples used by Lizardi et al. include homogenized posterior silk glands from larvae, homogenized dog pancreas, homogenized spinach leaves, and concentrated tissue culture cells.

Lizardi et al.'s method is a modification of the procedure described by Wilcockson, 66 Analytical Biochem, 64 (1975). In the abstract on page 64, Wilcockson says that "[t]he addition of an appropriate mixture of ethanol, water and sodium perchlorate to crude extracts of some biological material results in the selective precipitation of nucleic acids."

Wilcockson, 135 Biochem. J. 559 (1973), describes using sodium perchlorate for deproteinization during the extraction of nucleic acid from cells.

SUMMARY OF THE INVENTION

In general the invention features a method of extracting nucleic acids from a crude buffy coat fraction contained in an aqueous medium, typically, for example, whole blood the method including the steps of (1) treating the crude buffy coat fraction to break open the white blood cells contained therein to release the proteins and the nucleic acids in the cells into the aqueous medium;

(2) solubilizing the protein and the nucleic acids in the aqueous medium; and (3) precipitating the nucleic acids under conditions under which the proteins remain in solution.

The buffy coat fraction is the grayish layer, present after a blood sample is centrifuged, between the lower layer of red blood cells and the upper layer of clear serum. The buffy coat fraction includes a mixture of white blood cells, red blood cells, and serum; crude means that the buffy coat fraction is used directly in the method without further purification of the white blood cells and thus may have low contaminating levels of red blood cells and serum.

In preferred embodiments, the crude buffy coat fraction is treated with an agent that breaks open the white blood cells. The preferred agents are biological detergents such as SDS, LDS, NP40 triton, and sarcosyl; examples of other common biological detergents can be found in the 1987 Sigma Chemical Company Catalogue, pages 310-316. The detergents extract the proteins in cell membranes causing the membranes to break down.

In other preferred embodiments the method further includes the step of contacting the crude buffy coat fraction with a protein cleaving agent such as a proteinase. This step preferably is carried out simultaneous with or subsequent to the step of contacting the blood sample with the agent that breaks open the white blood cells. The protein cleaving agent shears those proteins released from the cells when the cells break open; the smaller, sheared proteins are more readily solubilized by the solubilizing substance.

In other preferred embodiments, the proteins and nucleic acids are solubilized by contacting the sample containing the broken open cells with a solubilizing agent. The preferred solubilizing agents are perchlorate ion and iodide ion.

In other preferred embodiments, the precipitation of the nucleic acids includes contacting the aqueous medium containing the dissolved proteins and nucleic acids with a lower alkyl alcohol (e.g., ethanol, isopropanol) and a perchlorate.

In other preferred embodiments, the nucleic acid is DNA, and the method further includes the step of spooling the precipitated DNA.

The invention provides a simple, quick procedure for extracting nucleic acid from blood.

Other features and advantages of the invention will be apparent from the following description of the preferred embodiments thereof and from the claims.

DESCRIPTION OF THE PREFERRED EMBODIMENTS

In the preferred method, the crude buffy coat fraction of blood is treated with a detergent-porteinase solution to break open the white blood cells and release the cells' proteins and nucleic acids. The resulting sample is treated with aqueous sodium perchlorate to dissolve the proteins and DNA. Subsequently the solution containing the proteins and DNA is treated with isopropanolic perchlorate to precipitate the DNA; most of the protein stays in solution. The precipitated DNA is spooled, and the spooled DNA is then used in any standard, nucleic acid hybridization assay.

To obtain the buffy coat fraction, a blood sample is centrifuged at 2000 rpm for ten minutes in a table top centrifuge, ideally comparable to an IEC Centra 7 (available through Damon, Needham Heights, Mass.). Three phases result, a clear upper phase (serum), a red lower phase (red blood cells), and the gray buffy coat fraction, which contains the white blood cells, in the middle. The clear upper phase is removed with a pipette, and the buffy coat fraction is drawn off.

To the buffy coat fraction is added an equal volume of 2× NETS buffer (4% SDS, 0.2M NaCl, 15 mM EDTA, 50 mM tris-HCl, pH 7.5) containing 700 µg/ml proteinase K. The mixture is incubated for 30 minutes at 37° C. During that time the cells are broken open by the SDS, which dissolves the proteins out of the cell membranes; the proteins are further cleaved by the proteinase K. At the end of the 30 minute period the solution has turned viscous.

To the viscous solution is added a 0.2 volume of 7M aqueous sodium perchlorate, and the resulting mixture is stirred for 1-2 minutes at 65° C. The aqueous perchlorate solubilizes the proteins and nucleic acid, and the solution turns clear.

To the clear solution is added an equal volume of isopropanolic perchlorate reagent (IPR; 4:4 saturated aqueous sodium perchlorate:saturated isopropanolic sodium perchlorate) with swirling; nucleic acid (DNA plus some RNA) begins to precipitate, leaving the proteins behind in solution. Three additional volumes of IPR (each volume being equal to the original volume of IPR added) are added. More nucleic acid precipitates.

The precipitated DNA is spooled to separate it from precipitated RNA.

For further purification, the DNA, which may contain unwanted salts and a small amount of residual protein, is dissolved in a buffer consisting of 10 mM tris-HCl (pH 8) and 1 mM EDTA, heating at 65° C. for 5-10 minutes if necessary. Sodium chloride is added to a final concentration of 0.18M. One volume of isopropanol is added, and the solution is mixed. The DNA that precipitates is spooled and resuspended overnight at 4° C. in a small amount of 10 mM tris HCl (pH8)—1 mM EDTA; the residual proteins and the contaminating salts stay behind in solution.

The spooled DNA can be used in any standard hybridization assay.

The preferred method can be carried out with a minimum amount of equipment, e.g., a fume hood is unnecessary, and is ideally suited for use in a genetic reference laboratory. The DNA is ready for further use overnight, and the procedure consumes less than one hour of total bench time. Moreover, the method can be carried out on many blood samples simultaneously and could potentially be automated.

OTHER EMBODIMENTS

Other embodiments are within the following claims. For example, other standard biological detergents can be used in place of SDS. Moreover, other solubilizing substances, e.g., chaotropic agents such as sodium iodide, can be used in place of the perchlorate ion.

IPR can be made from other perchlorate salts.

The four volumes of IPR that cause precipitation can be added at once instead of in separate one volume and three volume lots. Moreover, perchlorate in ethanol can be used as the precipitating agent, although it does not work quite as well as IPR, which keeps proteins in solution better to yield a cleaner DNA.

The DNA precipitation step can be carried out by contacting the solutions containing the dissolved DNA and protein first with a perchlorate salt and then with a lower alkyl alcohol, rather than with a solution consisting of a perchlorate salt dissolved in a lower alkyl alcohol (e.g., EPR). Moreover, when the solubilizing agent is aqueous perchlorate, precipitation can be done by adding only a lower alkyl alcohol, since the perchlorate, which holds the proteins in solution while the DNA precipitates, is already present.

Any nucleic acid present in the white blood cells, including, e.g., the nucleic acid of an AIDS virus that has invaded the cell, can be isolated using the above methods.

I claim:

1. A method of extracting nucleic acids from a crude buffy coat fraction in an aqueous medium, comprising the steps of:
    (a) first treating said crude buffy coat fraction with biological detergent means to cause white blood cells contained in said fraction to release proteins and nucleic acids contained within said cells into said aqueous medium;
    (b) solubilizing said proteins and said nucleic acids in said aqueous medium from step (a) by the addition of a solubilizing agent;
    (c) precipitating said solubilized nucleic acids of step (b) with a nucleic precipitating agent under conditions whereby said proteins remain in solution; and
    (d) spooling said precipitated nucleic acids.

2. The method of claim 1 further comprising the step of contacting said buffy coat fraction during or after said treating step with an agent selected from the group consisting of enzymes for cleaving said proteins.

3. The method of claim 1 wherein said solubilizing step comprises contacting said proteins and said nucleic acids in said aqueous medium with a solubilizing substance selected from the group consisting of perchlorate salt, iodide salt and a combination of perchlorate salt and iodide salt.

4. The method of claim 1 wherein said nucleic acid comprises DNA.

5. The method of claim 1 wherein said precipitating step comprises contacting said aqueous medium containing said solubilized proteins and nucleic acids with a lower alkyl alcohol and a perchlorate.

6. The method of claim 5 wherein said lower alkyl alcohol is ethanol.

7. The method of claim 5 wherein said lower alky alcohol is isopropanol.

* * * * *